United States Patent [19]

Trecker et al.

[11] 4,225,513

[45] * Sep. 30, 1980

[54] CATALYTIC DECARBONYLATION OF ESTERS

[75] Inventors: David J. Trecker, South Charleston; Michael R. Sandner, Charleston, both of W. Va.

[73] Assignee: Union Carbide Corporation, New York, N.Y.

[*] Notice: The portion of the term of this patent subsequent to Jun. 6, 1995, has been disclaimed.

[21] Appl. No.: 912,873

[22] Filed: Jun. 5, 1978

Related U.S. Application Data

[62] Division of Ser. No. 366,440, Jun. 4, 1973, Pat. No. 4,093,661.

[51] Int. Cl.$^3$ .............................................. C07C 45/41
[52] U.S. Cl. .................................................... 568/397
[58] Field of Search ............................ 260/601 R, 595

[56] References Cited

U.S. PATENT DOCUMENTS

| | | | |
|---|---|---|---|
| 1,892,742 | 1/1933 | Walter et al. | 260/595 |
| 1,926,632 | 9/1933 | Roka | 260/595 |
| 1,954,023 | 4/1934 | Oxley et al. | 260/595 |
| 1,988,021 | 1/1935 | Schmidt et al. | 260/595 |
| 2,108,156 | 2/1938 | Wortz | 260/595 |
| 2,697,729 | 12/1954 | Ohlson et al. | 260/595 |
| 3,075,016 | 1/1963 | Hammerberg et al. | 260/601 R |
| 4,093,661 | 6/1978 | Trecker et al. | 260/595 |

FOREIGN PATENT DOCUMENTS 1074265  7/1967  United Kingdom ................ 260/601 R

OTHER PUBLICATIONS

Matthews et al., "Jour. Org. Chem.", vol. 35, 1970, pp. 4158–4159.
Ipatieff et al., "Bull. Soc. Chim." (France), 1951, pp. 259–268.
Noto et al., "Trans. Faraday Soc.", vol. 63, Sep.–Dec., pp. 3081–3087, (1967).

*Primary Examiner*—Norman Morgenstern
*Attorney, Agent, or Firm*—Bernard Francis Crowe

[57] ABSTRACT

Lower alkanoate esters of alcohols are contacted in the vapor phase and at elevated temperatures with certain metal oxide catalysts to produce the aldehyde or ketone corresponding to said alcohol. Preferred catalysts include nickel oxide, zinc oxide and chromium oxide.

8 Claims, No Drawings

CATALYTIC DECARBONYLATION OF ESTERS

This application is a division of our prior U.S. application Ser. No. 366,440, filed June 4, 1973, now U.S. Pat. No. 4,093,661.

The invention relates to a process for the catalytic decarbonylation of lower alkanoate esters of primary or secondary alcohols, to form the aldehyde or ketone corresponding to the alcohol.

The vapor phase, catalytic dehydrogenation of primary and secondary alcohols to the corresponding aldehydes and ketones is known. For instance, see Wagner and Zook, "Synthetic Organic Chemistry", John Wiley & Sons (1953), Methods 159 (page 290) and 181 (page 325). However, in cases where the formate or other alkanoate esters of such alcohols were readily available (as from by-products of the oxo process), rather than the alcohol itself, the prior art was not aware of a vapor phase, catalytic process for producing the aldehydes and ketones directly from said esters. Rather, the intermediate step of producing the alcohol from the ester (as by hydrolysis) was considered necessary.

The present invention is based upon the discovery that aldehydes and ketones can be produced directly from lower alkanoate esters of alcohols by a vapor phase, catalytic process. The process of the invention comprises contacting a lower alkanoate ester of a primary or secondary alcohol, in the vapor phase, with a metal oxide catalyst, at an elevated temperature and for a period of time sufficient to produce the aldehyde or ketone corresponding to said alcohol.

The reactants employed in the process are lower alkanoate esters of primary or secondary alcohols. While the formate esters are preferred for use in the invention, other lower alkanoate esters, up to about $C_6$ alkanoate esters, can be employed. As the number of carbon atoms in the alkanoate portion of the ester increases, the temperature at which essentially complete conversion of the ester occurs increases.

The primary or secondary alcohol whose lower alkanoate esters are employed in the process, can be an aliphatic, cycloaliphatic, or heterocyclic alcohol. The alcohol can contain other substituent or functional groups which will not interfere with the reaction to any substantial degree. Illustrative examples of the substituent or functional groups that can be present include phenyl, hydroxyl, olefinic unsaturation, ether, and other thermally stable functional groups.

The alkanoate ester of a primary or secondary alcohol that is employed in this invention includes those that can be represented by Formula I:

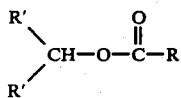

wherein R represents hydrogen or alkyl of up to 5 carbon atoms, and wherein each R' individually represents hydrogen; alkyl; alkenyl; phenyl; the two R' variables, along with the carbon atom to which they are attached, taken together to form (a) a cycloaliphatic group having 5 to 7 ring carbon atoms, (b) a heterocyclic group having 5 to 7 ring atoms, wherein the hetero atom(s) can be oxygen or nitrogen, and (c) a norbornyl group.

Specific illustrative lower alkanoate esters of primary and secondary alcohols that can be employed in the process of the invention include alkyl esters such as methyl formate, methyl acetate, methyl butyrate, ethyl formate, ethyl propionate, ethyl valerate, n-propyl formate, isopropyl formate, n-butyl formate, n-butyl acetate, n-butyl caproate, 2-butyl formate, 2-methyl-n-propyl formate, n-pentyl formate, 2-pentyl formate, 3-pentyl formate, n-pentyl acetate, 2-hexyl formate, 3-hexyl formate, n-hexyl formate, 2-ethylhexyl formate, 2-ethylhexyl acetate, n-octyl formate, n-decyl formate, lauryl formate and myristyl formate.

Cycloalkyl esters can also be employed, including as illustrations, cyclopentyl formate, cyclohexyl formate, cyclohexyl acetate, 2-exo-norborynl formate, 2-exo-norbornyl acetate, cycloheptyl formate, 8-exotricyclo [5.2.1.0$^{2,6}$] decyl formate, cycloheptyl acetate, and methylcyclohexyl formate. Other esters that can be used include benzyl formate, benzyl acetate, phenethyl formate, phenethyl acetate, allyl acetate, 2-methyl-2-propenyl acetate, and cyclohex-3-enyl formate.

The alcohol moiety of the ester will ordinarily contain not more than 14 carbon atoms, and preferably not more than 10 carbon atoms. While higher alcohols would be operative, they tend to be difficult to volatilize, and therefore require the use of very low pressures, volatile cosolvents, and/or very high temperatures, which are disadvantages in commercial scale operations.

The product of the invention is the aldehyde or ketone corresponding to the alcohol moiety of the ester reactant. Thus, when an ester that can be represented by Formula I is employed as the reactant, the aldehyde or ketone product will be represented by Formula II:

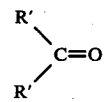

wherein each R' individually has the meaning stated above with respect to Formula I.

The ester can be mixed with a diluent that does not interfere with the process. Such diluents include alcohols, aldehydes, ketones, olefins, formaldehyde, formic acid and other organic acids, water, aromatic hydrocarbons, aliphatic hydrocarbons, amines, and other esters. Because a wide variety of other materials can be present, the feed material need not be highly purified prior to being employed in the process of the invention. This is an economic advantage when the feed for this process is composed of a byproduct stream from another process, such as an oxo process.

It is desirable to include hydrogen gas in the feed stream in order to lengthen the useful life of the catalyst.

The catalysts that are employed in the invention are Period 4 metal oxides such as the oxides of zinc, nickel, copper, chromium, titanium, vanadium, manganese, iron, and cobalt. The preferred catalysts are oxides of nickel, zinc, and chromium.

The catalyst can be supported on an inert catalyst support such as alumina, silica, mixtures thereof, carbon, or other inert catalyst support.

The process of the invention is best carried out by continuously passing the ester reactant, in the vapor phase, through a bed of the catalyst. It is therefore not appropriate to discuss catalyst proportions. Rather, the ester reactant is maintained in contact with the catalyst for a period of time sufficient to produce the aldehyde or ketone corresponding to the alcohol moiety of the ester. This contact time is not narrowly critical. For example, the contact time can vary over a range of from about 0.1 to about 300 seconds, preferably from about 0.5 to about 150 seconds, and more preferably from about 2 to about 60 seconds.

The pressure under which the process is carried out is also not narrowly critical. Convenient pressures are found within the range of from about 0.1 to about 10 atmospheres, and preferably from about 0.5 to about 2 atmospheres.

The process is carried out at elevated temperatures sufficient to maintain the feed stream in the vapor phase, and to produce the desired aldehyde or ketone, but not so high that significant amounts of pyrolysis products are produced. Broadly, satisfactory temperatures are found within the range of from about 250° to about 550° C., preferably from about 280° to about 480° C. and more preferably from about 300° to about 430° C. The desired temperature can be maintained by conventional means such as by using a preheater to vaporize the feed stream, and then by employing a heated catalyst bed. The exact temperature selected may vary somewhat with such factors as nature of reactants and nature of catalyst, as will be illustrated below in the Examples.

The aldehyde or ketone product can be recovered by conventional methods from the product stream after it has passed through the catalyst bed. For example, fractional distillation can be used to recover the product from by-products and other components of the reaction mixture.

The Examples set forth below illustrate the practice of the invention. All parts or percentages are by weight, unless otherwise indicated.

EXPERIMENTAL PROCEDURE

Materials

The following chemicals were obtained from commercial sources: exo-2-norbornyl alcohol, 2-norbornanone, 2- and 3-hexanol, 2- and 3-hexanone, 1-hexene, cyclohexene, t-butyl alcohol, benzyl alcohol, benzene, toluene, cyclohexanol, n-hexyl formate, 1-octanol, 2-hexene, acetone, 2-ethylhexaldehyde, dicyclopentadiene, dicyclopentadiene hydrate, 2-propanol, crude 3-butyl formate, and benzaldehyde.

The following compounds were prepared by the methods listed and were used as feed or for comparison purposes: t-butyl formate and benzyl formate mixture were prepared by the method of Stevens and Van Es;[1] cyclohexyl formate and exo-norbornyl formate were prepared by the addition of formic acid to the corresponding olefins;[2] exo-norbornyl acetate were prepared by the method of Winstein and Trifan;[3] cyclohexyl acetate were prepared by treatment of cyclohexanol with acetic anhydride/pyridine and product identity confirmed by comparison of infrared spectra;[4] dicyclopentenyl formate and dihydrodicyclopentenyl formate (8-tricyclo [5.2.1.0$^{2.6}$] decyl formate) were prepared by the method of Bergmann and Japhe;[5] dicyclopentenyl ketone, 8-hydroxy-tricyclo [5.2.1.0$^{2.6}$] decane and tricyclo [5.2.1.0$^{2.6}$] decan-8-one were prepared by the method of Brunson and Riener;[6] and crude 3-pentyl formate was identified by a combination of VPC-mass spectroscopy.

(1) W. Stevens and A. Van Es, Rec. Tran, Chim., 83, 1287 (1964).
(2) D. C. Kleinfelter and P. nov R. Schleyer, "Org. Syn.", 42, 79 (1962).
(3) S. Winstein and D. Trifan, J. Am. Chem. Soc., 74, 1154 (1952).
(4) Infrared spectra for comparative purposes were taken from collections of spectra in "Documentation of Molecular Spectroscopy". Butterworths Scientific Publications, London or "Sadtler Standard Spectra", Sadtler Research Laboratories, Inc. Philadelphia, Pa. An alternate method involved comparison with spectra or commercial materials.
(5) F. Bergman and H. Japhe, J. Am. Chem. Soc., 69, 1826 (1947).
(6) H. A. Bruson and T. W. Riener, J. Am. Chem. Soc., 67, 723 (1945).

Analytical Methods

Materials were analyzed by vpc analysis using one or both of the following columns: a 10 ft.×¼ in. column packed with 10 percent "W-98" silicone oil on "Chromasorb G" carrier (60/80 mesh) or a 10 ft.×¼ in. column packed with 15 percent "FFAP" on "Chromasorb W" carrier (60/80 mesh). Comparison of retention times with those of authentic materials was employed where required. Further analyses by infrared or mass spectroscopy were used as required.

Equipment

The connecting tubing, pre-heater, condensing system and reactor chamber were constructed of stainless steel or glass. The reactor chamber was 1 inch in diameter by 25 inches long, and was heated electrically or by a "Dow-Therm" jacket. The pre-heater system was heated electrically. Liquid solutions were fed to the system by means of a bellows pump.

Catalysts

The catalysts employed had the following compositions (the percentages are based on weight of catalyst plus support):

Catalyst A
Copper (as the oxide), 13.84 percent, with minor amounts (less than one percent) of chromium, as the oxide, supported on a silica support;

Catalyst B
Nickel (as the oxide), 12.49 percent, with minor amounts (less than 0.5 percent each) of the oxides of chromium, iron, and copper, supported on a silicaalumina support containing 84 percent alumina, 11 percent silica, the remainder being oxides of iron, titanium, calcium, barium, potassium, and sodium;

Catalyst C
Zinc oxide, 79 percent, calcium oxide, 7 percent; potassium oxide, 3 percent; aluminum oxide, 5 percent, and oxides and sulfates of chromium, about 6 percent;

Catalyst D
Nickel (as the oxide) 13.54 percent, the remainder being minor amounts (less than 0.5 percent each) of the oxides of chromium, sodium, and potassium, supported on the same support as Catalyst B. The catalyst also contained 0.35 percent sulfate.

Typical Procedure

A solution of the feed compound in a suitable solvent, or the neat compound, was pumped to the pre-heater system and a small flow of hydrogen was used as a carrier gas at all times. Liquid feed rates were on the order of 50–70 milliliters/hour, and residence times of the feed in the catalyst bed were on the order of 10–18 seconds. The pressure in the systems was approximately atmospheric. The cooled effluent from the reactor system was then analyzed as described previously.

The Tables below display the results of these experiments.

TABLE I

| Example | FEED Compound | Wt. % | Catalyst | Temp. °C. | PRODUCT COMPOSITION Compound | Glc Analysis, % |
|---|---|---|---|---|---|---|
| 1 | 2-exo-Norbornanol toluene (control) | 60 40 | A | 280–300 | 2-exo-Norbornanol 2-Norbornanone | 13 87 |
| 2 | 2-exo-Norbornyl formate toluene | 50 50 | A | 280–300 | 2-exo-Norbornyl formate 2-exo-Norbornanol 2-exo-Norbornanone | 9 6 85 |
| 3 | 2-exo-Norbornyl formate Benzene | 46 54 | A | 300–320 | 2-exo-Norbornyl formate 2-exo-Norbornanol 2-Norbornanone | 14 80 6 |
| 4 | Cyclohexyl formate Benzene | 30 70 | A | 280–300 | Cyclohexyl formate Cyclohexanol Cyclohexanone | 35 4 40 |
| 5 | Cyclohexyl formate Benzene | 46 54 | A | 300–320 | Cyclohexyl formate Cyclohexanol Cyclohexanone | 8 80 12 |
| 6 | 1-Hexanol (control) | 100 | A | 310–320 | 1-Hexanol n-Hexaldehyde | 60 40 |
| 7 | 1-Hexyl formate Benzene | 46 54 | A | 300–320 | 1-Hexyl formate 1-Hexanol n-Hexaldehyde | 5 87 8 |
| 8 | 2-Hexyl formate and 3-Hexyl formate Benzene | 19 11 70 | A | 280–300 | Total formates 2-Hexanone 3-Hexanone | 4 62 34 |
| 9 | 3-Pentyl formate 3-pentanol Benzene | 11 9 70 | A | 280–300 | 3-Pentyl formate 3-Pentanol 3-Pentanone | 35 1.5 63.5 |
| 10 | Benzyl formate Benzyl acetate Benzyl alcohol n-Hexane | 37 4 6 53 | A | 320–340 | Benzyl formate Benzyl acetate Benzyl alcohol Benzaldehyde Toluene Benzene | 0.5 6.7 34.2 29.1 11.3 18.2 |
| 11 | 2-exo-Norbornyl acetate Benzene | 30 70 | A | 280–300 | Recovered unchanged | |
| 12 | Cyclohexyl acetate Benzene | 30 70 | A | 280–300 | Recovered unchanged | |
| 13 | 2-Ethylhexaldehyde Benzene | 30 70 | A | 280–300 | Recovered unchanged | |
| 14 | 2-Propanol (control) | 100 | C | 350 | 2-propanol acetone | 89.5 10.5 |
| 15 | 2-Propanol (control) | 100 | C | 420–430 | 2-propanol acetone | 5 95 |
| 16 | 3-Pentyl formate 3-pentanol 3-pentanone | 63 20 17 | C | 340 | 3-Pentyl formate 3-Pentanol 3-Pentanone | 6 37 57 |
| 17 | 3-Pentyl formate 3-Pentanol 3-Pentanone | 63 20 17 | C | 390–410 | 3-Pentanol 3-Pentanone | 20 80 |
| 18 | Cyclohexanol (control) Benzene | 44 56 | C | 400–420 | Cyclohexanone | 100 |
| 19 | Cyclohexyl formate Benzene | 44 56 | C | 400–420 | Cyclohexanone Phenol | 90 10 |
| 20 | Cyclohexyl acetate Benzene | 44 56 | C | 400–420 | Cyclohexanone Cyclohexene Phenol | 60 31 9 |
| 21 | 2-exo-Norbornyl formate Benzene | 30 70 | C | 400–420 | 2-Norbornanone | 100 |
| 22 | 2-exo-Norbornyl acetate Benzene | 30 70 | C | 400–420 | 2-Norbornanone Norbornene | 90 10 |
| 23 | 8-exo-Tricyclo[5.2.1.0$^{2,6}$] decyl formate Benzene | 30 70 | C | 400–420 | 8-oxo-Tricyclo[5.2.1.0$^{2,6}$] decyl formate Tricyclo[5.2.1.0$^{2,6}$]decan-8-one | 2 92 |
| 24 | 1-Hexyl formate Benzene | 30 70 | C | 400–420 | 1-Hexyl formate n-Hexanol n-Hexaldehyde 1-Hexene | 15 4 71 10 |
| 25 | 2-Propanol (control) | 100 | B | 320–340 | 2-Propanol acetone | 67 33 |
| 26 | Cyclohexyl formate Benzene | 46 54 | B | 330–340 | Cyclohexanol Cyclohexanone | 15 85 |
| 27 | Cyclohexyl acetate | 100 | B | 320–340 | Recovered unchanged | |
| 28 | 2-oxo-Norbornyl formate Benzene | 46 54 | B | 330–340 | 2-exo-Norbornanol 2-Norbornanone | 34 66 |

TABLE I-continued

| Example | FEED Compound | Wt. % | Catalyst | Temp. °C. | PRODUCT COMPOSITION Compound | Glc Analysis, % |
|---|---|---|---|---|---|---|
| 29 | 3-Pentyl formate | 63 | B | 320–340 | 3-Pentanol | 40 |
|  | 3-Pentanol | 20 |  |  | 3-Pentanone | 60 |
|  | 3-Pentanone | 17 |  |  |  |  |
| 30 | Benzyl formate | 37 | B | 320–340 | Benzyl acetate | 9 |
|  | Benzyl acetate | 4 |  |  | Benzyl alcohol | 43 |
|  | Benzyl alcohol | 6 |  |  | Benzaldehyde | 34 |
|  | Hexane | 53 |  |  | Toluene | 7 |
|  |  |  |  |  | Benzene | 7 |
| 31 | Benzyl acetate | 46 | B | 300–320 | Recovered unchanged |  |
|  | hexane | 54 |  |  |  |  |
| 32 | 3-Pentyl formate | 63 | D | 355–365 | 3-Pentyl formate | 5.3 |
|  | 3-Pentanol | 20 |  |  | 3-Pentanol | 41.4 |
|  | 3-Pentanone | 17 |  |  | 3-Pentanone | 53.3 |
| 33 | 3-Pentyl formate | 63 | D | 373–382 | 3-Pentyl formate | 0 [a] |
|  | 3-Pentanol | 20 |  |  | 3-Pentanol | 26.2 |
|  | 3-Pentanone | 17 |  |  | 3-Pentanone | 73.8 |
| 34 | 3-Pentyl formate | 63 | D | 394–398 | 3-Pentyl formate | 0 |
|  | 3-Pentanol | 20 |  |  | 3-Pentanol | 3.0 |
|  | 3-Pentanone | 17 |  |  | 3-Pentanone | 97.0 |
| 35 | 3-pentyl formate | 63 | D | 400–410 | 3-pentyl formate | 0 |
|  | 3-pentanol | 20 |  |  | 3-pentanol | <1 |
|  | 3-pentanone | 17 |  |  | 3-pentanone | 99 |
| 36 | Cyclohexanol | 50 | D | 372–385 | Cyclohexanol | 0 |
|  | Toluene | 50 |  |  | Cyclohexanone | 5.8 |
|  |  |  |  |  | Phenol | 83.2 |
|  |  |  |  |  | Benzene | 11.0 |

[a] Distillation of the reaction mixture resulted in the isolation of 3-pentanone and 3-pentanol in a yield of 72%.

As is illustrated in the Examples, the exact reaction temperature selected will be dependent, in part, upon the nature of the reactant, nature of the catalyst, and composition of the product that is desired. As a general rule, for any given catalyst and ester, as the temperature increases, the percentage conversion of the ester increases, and the proportion of ketone or aldehyde to alcohol in the product also increases. This general rule is especially well illustrated in Examples 32–36.

The copper-containing catalyst (catalyst A) cannot be used at temperatures much above 300°–320° C., because it tends to sinter. The other catalysts that are exemplified can be used at much higher temperatures, and would therefore be the ones selected, for instance, when acetate or higher alkanoate esters are used, because such esters require higher temperatures than the formates. This principle is illustrated in the comparison of Examples 10–12, on the one hand, with Examples 20 and 22, on the other. Also, Examples 27, 30, and 31 illustrate reaction temperatures that were too low to convert the acetates.

What is claimed is:

1. A vapor phase process for the production of ketones, which comprises contacting a formate of a secondary alkyl alcohol, in the vapor phase, with an oxide of a metal selected from the group consisting of nickel, chromium, zinc, copper, manganese, cobalt, iron, titanium, and vanadium, at a temperature of 280–420° C. and for a period of time sufficient to decarbonylate said formate and produce the ketone corresponding to said secondary alkyl alcohol.

2. The process claimed in claim 1 wherein the lower alkanoate ester is 2-butyl formate.

3. The process claimed in claim 1 wherein the lower alkanoate ester is 2-pentyl formate.

4. The process claimed in claim 1 wherein the lower alkanoate ester is 3-pentyl formate.

5. The process claimed in claim 1 wherein the lower alkanoate ester is 2-hexyl formate.

6. The process claimed in claim 1 wherein the lower alkanoate ester is 3-hexyl formate.

7. The process claimed in claim 1 wherein the lower alkanoate ester is 2-ethylhexyl formate.

8. The process claimed in claim 1 wherein the lower alkanoate ester is 2-ethylhexyl acetate.

* * * * *